(12) United States Patent
Auer et al.

(10) Patent No.: US 7,241,365 B2
(45) Date of Patent: Jul. 10, 2007

(54) MATERIAL FOR A FACILITY FOR THE PRODUCTION OF ANHYDROUS FORMIC ACID

(75) Inventors: Heinz Auer, Neulussheim (DE); Bernd Bessling, Grosse Ille, MI (US); Hans Hammer, Mannheim (DE); Hans Hasse, Kaiserslautern (DE); Friedrich Sauer, Obersülzen (DE); Maximilian Vicari, Limburgerhof (DE); Gerhard Wagner, Ludwigshafen (DE); Till Adrian, Bobenheim-Roxheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/181,814

(22) PCT Filed: Jan. 24, 2001

(86) PCT No.: PCT/EP01/00748

§ 371 (c)(1),
(2), (4) Date: Jul. 23, 2002

(87) PCT Pub. No.: WO01/55077

PCT Pub. Date: Aug. 2, 2001

(65) Prior Publication Data

US 2003/0116423 A1    Jun. 26, 2003

(30) Foreign Application Priority Data

Jan. 24, 2000    (DE) .................................. 100 02 795

(51) Int. Cl.
*B01D 3/34*      (2006.01)
*C07C 53/06*    (2006.01)
*C22C 19/05*    (2006.01)
*C22C 30/00*    (2006.01)

(52) U.S. Cl. .................. 203/15; 202/155; 202/169; 202/267.1; 203/43; 203/46; 203/60; 203/71; 203/86; 420/586; 562/609

(58) Field of Classification Search .............. 203/15, 203/46, 60, 71, 86, 43; 202/153–155, 172, 202/267.1, 168–170; 420/586, 590; 562/609
See application file for complete search history.

(56) References Cited

U.S. PATENT DOCUMENTS

| | | | | |
|---|---|---|---|---|
| 3,960,671 A | * | 6/1976 | Clovis et al. ................ 203/7 |
| 4,008,344 A | | 2/1977 | Okamoto .................... 427/307 |
| 4,326,073 A | | 4/1982 | Wolf et al. ................ 562/609 |
| 4,380,663 A | | 4/1983 | Roscher et al. ............ 562/536 |
| 4,415,532 A | | 11/1983 | Crook ........................ 420/585 |
| 5,338,508 A | * | 8/1994 | Nitta et al. ................ 420/120 |

FOREIGN PATENT DOCUMENTS

| | | |
|---|---|---|
| EP | 2513678 | 10/1976 |
| EP | 017866  | 10/1980 |
| EP | 717028  | 6/1996 |

OTHER PUBLICATIONS

Zaritskii, *Khimicheskoe i Neft. Mash.*, No. 7, pp. 24-25, Jul. 1990.
*Chem. Abst.*, 105:26, Dec. 29, 1986.
*Chem. Abst.*, 107:12, Sep. 21, 1987.
Schillmoller, *Chem. Eng. Progress*, p. 66-71, Feb. 1997.
Gassen et al., *Z. Werkstofftech*, 17, 1986, p. 218-225.
Outlook, Teledyne Vah Cheng, Albany, Winter/Spring 1990, vol. 11, No. 1.
Yau et al., *Chem Eng. Progress*, p. 42-46, Jan. 1995.
Yau et al., *Chem Eng. Progress*, p. 65-69, Feb. 1992.

* cited by examiner

*Primary Examiner*—Virginia Manoharan
(74) *Attorney, Agent, or Firm*—Novak Druce & Quigg, LLP

(57) ABSTRACT

The invention relates to an apparatus and a process for the preparation of anhydrous or substantially anhydrous formic acid. This apparatus is constructed partly or entirely of substantially zirconium-free materials. The extractant employed is a liquid of the general formula I

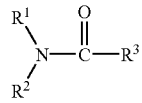 (I)

Figure 1:
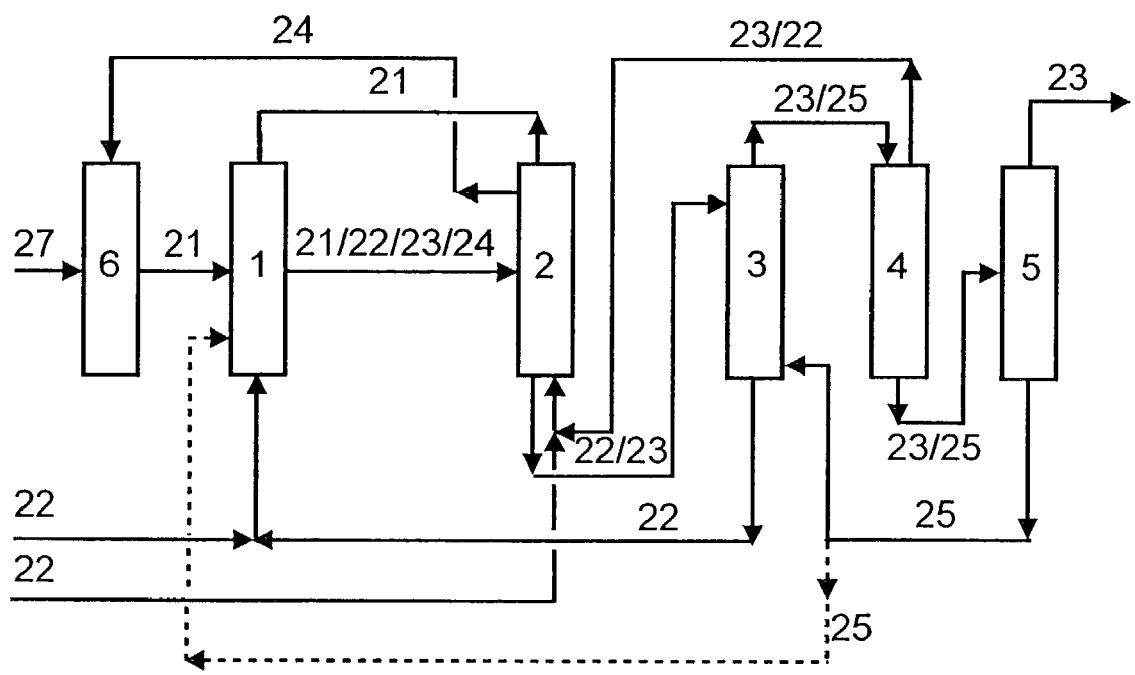

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group. The apparatus has a synthesis reactor (6), a hydrolysis reactor (1), three distillation devices (2,4,5) and an extraction device (3).

10 Claims, 2 Drawing Sheets

MATERIAL FOR A FACILITY FOR THE PRODUCTION OF ANHYDROUS FORMIC ACID

The invention relates to an apparatus and a process for obtaining anhydrous or substantially anhydrous formic acid, and to the use of certain classes of material as construction materials for this apparatus.

EP-B 0 017 866 discloses that anhydrous or substantially anhydrous formic acid is obtained if
a) methyl formate is subjected to hydrolysis,
b) methanol and excess methyl formate are distilled off from the resultant hydrolysis mixture,
c) the bottom product from the distillation (b), which comprises formic acid and water, is extracted in a liquid-liquid extraction with an extractant which principally takes up the formic acid,
d) the resultant extract phase, comprising formic acid and some of the water, is subjected to distillation,
e) the top product obtained in this distillation, which comprises water and some of the formic acid, is fed back into the lower part of a distillation device in step (b),
f) the bottom product from distillation step (d), which predominantly comprises extractant and formic acid, is separated into anhydrous or substantially anhydrous formic acid and the extractant by distillation, and
g) the extractant leaving step (f) is fed back into the process.

To carry out this process, an apparatus is then provided which comprises the following elements:
a synthesis reactor for the preparation of methyl formate,
a hydrolysis reactor for the hydrolysis of methyl formate,
a distillation device for the separation of excess methanol and excess methyl formate from the hydrolysis mixture (step b)),
a distillation device for the distillation of an extract phase comprising formic acid, extractant and some of the water (step d)),
an extraction device for carrying out step c), and
a distillation device for the distillative separation of a mixture comprising predominantly extractant and formic acid into anhydrous or substantially anhydrous formic acid and extractant (step f)).

It is vital that the corresponding elements of the apparatus which come into contact with formic acid must be constructed of materials which are corrosion-resistant. Formic acid, in particular aqueous formic acid, is an extremely corrosive material. The term "corrosion" is taken to mean the interaction of a material with its environment which causes a measurable change in the material and results in an impairment of the function of the corresponding component or of the entire system. The term "corrosion" is thus taken to mean the disadvantageous and quality-reducing change in a material starting from the surface and caused by unintended chemical or electrochemical attacks. The attacking agent, which acts chemically or electrochemically, is known as a corrosive agent—formic acid, in particular aqueous formic acid, is regarded as a highly corrosive agent.

Plants for the preparation of formic acid or aqueous formic acid must therefore be protected against corrosion to a particular extent. Only a few materials are suitable as construction material for the plant parts which come into contact with formic acid. In the literature [T.-L. Yau, K. W. Bird, Chemical Engineering Process, January 1992, page 65], [T.-L. Yau, K. W. Bird, Chemical Engineering Process, January 1995, page 42], [Company Information: "Outlook", Teledyne Vah Chang Albany, Winter/Spring 1990 Volume 11, No. 1, pages 1–3] exclusively zirconium and zirconium alloys containing at least 90% of zirconium are recommended as materials for this purpose. On contact with formic acid, zirconium is passivated—forms a stable oxidic protective layer. Other materials are less suitable, or suitable materials (apart from zirconium) are so expensive that they cannot be employed economically. Thus, industrial plant parts which come into contact with formic acid are generally made exclusively of zirconium or zirconium alloys containing at least 90% of zirconium. It is disadvantageous that zirconium-rich materials are expensive, and the investment costs of corresponding plant parts are therefore high.

It is an object of the present invention to provide an apparatus with which the above-mentioned process for the preparation of anhydrous or substantially anhydrous formic acid can be carried out. The material costs for the construction of the apparatus in question should be lower than comparatively for a corresponding apparatus constructed of zirconium-rich materials.

We have found that this object is achieved by an apparatus for obtaining anhydrous or substantially anhydrous formic acid, comprising
i) a synthesis reactor for the preparation of methyl formate,
ii) a hydrolysis reactor for the hydrolysis of methyl formate,
iii) a distillation device for the separation of excess methanol and excess methyl formate from the hydrolysis mixture,
iv) a distillation device for the distillation of an extract phase comprising formic acid, extractant and some of the water,
v) an extraction device, and
vi) a distillation device for the distillative separation of a mixture comprising predominantly extractant and formic acid into anhydrous or substantially anhydrous formic acid and extractant, where the extractant employed is a carboxamide of the general formula I

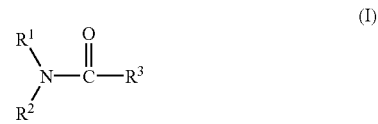

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group.

Thus, the apparatus according to the invention is characterized in that the devices ii), iii), iv), v) and/or vi) are constructed partly or entirely of a low-zirconium material selected from the group consisting of the material classes titanium/palladium alloys, chromium-, molybdenum- and/or tungsten-containing nickel-based materials and molybdenum-containing, highly alloyed, austenitic chromium/nickel special steels. The term "low-zirconium material" is taken to mean a material which contains less than 10% by weight, preferably less than 1% by weight, of zirconium.

Examples for chromium-, molybdenum- and/or tungsten-containing nickel-based materials are materials containing 14 to 24% by weight of Cr, 8 to 17% by weight of Mo and/or 3 to 5% by weight of W, max. 25% by weight of other elements and Ni as rest.

Examples for molybdenum-containing, highly alloyed, austenitic chromium/nickel special steels are steels containing 18 to 30% by weight of Cr, 12 to 40% by weight of Ni, 3 to 7% by weight of Mo, max. 3% by weight of Cu, max. 0.05% by weight of C, max. 25% by weight of other elements and Fe as rest.

These both groups of material are essential for the invention.

Examples for titanium/palladium alloys are alloys containing 0.1 to 0.25% by weight of Pd, max. 0.4% by weight of oxygen, max. 0.5% by weight of Fe, max. 1% by weight of any other element and Ti as rest. The total amount of all other elements—conventional additives, which are added during preparation of the alloys, and impurities—is max. 2% by weight related to the total composition of the alloy. In this kind of material class titanium/palladium alloys of this constitution are preferred.

If said alloys have counterparts with a different name, these are also included if they have a comparable composition and properties.

The term "substantially anhydrous formic acid" is taken to mean formic acid which contains a maximum of 30% by weight, preferably a maximum of 15% by weight, of water. The term "synthesis reactor" is taken to mean a device in which firstly the synthesis of methyl formate is carried out (usually in a corresponding reactor) and secondly, if desired, separation of the resultant synthesis mixture is carried out (usually in a distillation device downstream of the reactor). Suitable hydrolysis reactors are any desired reactors which can be employed for the hydrolysis of methyl formate. The extraction device employed is preferably a liquid-liquid extraction column. Suitable distillation devices are, in particular, distillation columns.

In the tables below, suitable classes of material (classes I to III) are defined in detail. The term "other elements" is taken to mean selectively added other elements as well as conventional additives, which are added during preparation, and impurities.

TABLE 1

| Class I | Class II | Class III |
| --- | --- | --- |
| Titanium/palladium alloys | Chromium-, molybdenum- and/or tungsten-containing nickel-based materials | Molybdenum-containing, highly alloyed, austenitic chromium/nickel special steels |

TABLE 2

| Class I Titanium/palladium alloys | | | | |
| --- | --- | --- | --- | --- |
| Characteristic alloy composition (principal elements) | Palladium: 0.1–0.25% by weight<br>Oxygen: max. 0.4% by weight<br>Iron: max. 0.5% by weight<br>Other elements: each max. 1% by weight, total max. 2% by weight;<br>corresponding to the materials/standards mentioned below Rest (basis material): titanium | | | |
| Examples | Country | Abbreviated name | Material No. | Standard |
| | D | Ti1Pd | 3.7225 | DIN 17851 |
| | | Ti2Pd | 3.7235 | DIN 17851 |
| | | Ti3Pd | 3.7255 | DIN 17851 |
| | USA | TiPd grade 7 | UNS R52400 | ASTM B265, B337, B338, B348, B381 |
| | | TiPd grade 11 | UNS R52250 | ASTM B265, B337, B338, B348, B381 |

TABLE 3

| Class II Chromium-, molybdenum- and/or tungsten-containing nickel-based materials | | | | |
| --- | --- | --- | --- | --- |
| Characteristic alloy composition (principal elements) | Chromium: 14–24% by weight<br>Molybdenum: 8–17% by weight and/or tungsten: 3–5% by weight<br>Other elements: each max. 10% by weight, total max. 25% by weight; for examples see below<br>Rest (basis material): nickel | | | |
| Examples | Country | Abbreviated name | Material No. | Standard |
| | D | NiMo16Cr15W | 2.4819 | DIN 17744 |
| | USA | Alloy C-276 | UNS N10276 | ASTM B366, B564, B574, B575, B619, B622, B626 |
| | D | NiCr22Mo9Nb | 2.4856 | DIN 17744, EN 10095 |
| | USA | Alloy 625 | UNS N06625 | ASTM B366, B443, B444, B446, B704, B705 |
| | D | NiMo16Cr16Ti | 2.4610 | DIN 17744 |
| | USA | Alloy-C4 | UNS N06455 | ASTM B574, B575, B619, B622, B626 |
| | D | NiCr23Mo16Al | 2.4605 | VdTUV materials sheet 505 |
| | USA | Alloy 59 | UNS N06059 | ASTM B622, B619, B626, B575, B574, B564 |
| | D | NiCr21Mo16W | 2.4606 | VdTUV materials sheet 515 |
| | USA | Alloy 686 | UNS N06686 | ASTM B564, B574, B575, B619, B622, B626 |
| | D | NiCr23Mo16Cu | 2.4606 | not yet standardized |
| | USA | Alloy C2000 (Hastelloy® C-2000® alloy) | | not yet standardized |

TABLE 4

|  | Class III<br>Molybdenum-containing, highly alloyed, austenitic chromium/nickel special steels | | | |
|---|---|---|---|---|
| Characteristic alloy composition (principal elements) | Chromium: 18–30% by weight<br>Nickel: 12–40% by weight<br>Molybdenum: 3–7% by weight<br>Copper: max. 3% by weight<br>Carbon: max. 0.05% by weight<br>Other elements: each max. 10% by weight,<br>total max. 25% by weight; for examples see below<br>Rest (basis material): iron | | | |
| Examples | Country | Abbreviated name | Material No. | Standard |
|  | D | X2NiCrMoN 17-13-5 | 1.4439 | EN 10088-1-2-3, DIN 17440, DIN 17441 |
|  | D | X1NiCrMoCuN 25-20-7 | 1.4529 | EN 10088-1-2-3 |
|  | D | X1NiCrMoCu 25-20-5 | 1.4539 | EN 10088-1-2-3 |
|  | USA |  | UNS N08904 | ASTM A240, A480, B625, B649, B673, B674, B677 |
|  | D | X1CrNiMoCuN 20-18-7 | 1.4547 | EN 10088-1-2-3 |
|  | USA |  | UNS S31254 | ASTM A182, A193, A194, A204, A249, A269, A276, A312, A358, A403, A409, A479, A813, A814 |
|  | USA |  | UNS S31725 | ASTM A167, A182, A213, A240, A249, A269, A276, A312, A358, A376, A409, A479 |
|  | USA |  | UNS S31726 | ASTM A167, A182, A213, A240, A249, A269, A276, A312, A358, A376, A409, A479 |

Precise concentration data for examples from the three classes of material indicated

TABLE 5

Class 1: Material number 3.7235
Chemical composition in % by weight

|  |  |  |  |  |  |  | Others | | |
|---|---|---|---|---|---|---|---|---|---|
|  | Fe | O | N | C | H | Pd | Individually | Together | Ti |
| Min |  |  |  |  |  | 0.15 |  |  | Basis |
| Max | 0.20 | 0.18 | 0.05 | 0.06 | 0.013 | 0.25 | 0.1 | 0.4 | Basis |

TABLE 6

Class 2: Material number 2.4819
Chemical composition in % by weight

|  |  |  |  |  |  |  |  |  | Others (V, Cu, W, Fe etc.) | | |
|---|---|---|---|---|---|---|---|---|---|---|---|
|  | C | Si | Mn | P | S | Co | Cr | Mo | Individually | Together | Ni |
| Min |  |  |  |  |  |  | 14.5 | 15.0 |  |  | Basis |
| Max | 0.015 | 0.08 | 1.0 | 0.025 | 0.015 | 2.5 | 16.5 | 17.0 | 7.0 | 13.0 |  |

TABLE 7

Class 2: Material number 2.4856
Chemical composition in % by weight

| | C | Si | Mn | P | S | Al | Co | Cr | Mo | Others (Cu, Nb, Ti, Fe etc.) Individually | Together | Ni |
|---|---|---|---|---|---|---|---|---|---|---|---|---|
| Min | 0.03 | | | | | | | 20.0 | 8.0 | | | Basis (58.0) |
| Max | 0.10 | 0.5 | 0.5 | 0.020 | 0.015 | 0.40 | 1.0 | 23.0 | 10.0 | 5.0 | 10.0 | |

TABLE 8

Class 3: Material number 1.4439
Chemical composition in % by weight

| | C | Si | Mn | P | S | N | Cr | Mo | Ni | Fe |
|---|---|---|---|---|---|---|---|---|---|---|
| Min | | | | | | 0.12 | 16.5 | 4.0 | 12.5 | Basis |
| Max | 0.030 | 1.0 | 2.0 | 0.045 | 0.015 | 0.22 | 18.5 | 5.0 | 14.5 | |

The extractant employed acts as corrosion inhibitor on contact of the above mentioned classes of material with aqueous formic acid.

The low-zirconium classes of material which are suitable are significantly cheaper than the materials recommended in the prior art, which have a high content of zirconium. The construction costs of an apparatus according to the invention for the preparation of anhydrous or substantially anhydrous formic acid are thus comparatively favorable.

In general, at least the surfaces of devices ii), iii), iv), v) and/or vi) which come into contact with formic acid and the extractant are constructed of the low-zirconium material—the term "surface" in this connection is taken to mean an external thin layer, preferably with a thickness of about 1 mm.

Said surfaces usually come into contact with media containing at least 1% of formic acid and at least 1%, preferably 5%, of extractant.

In the plant parts which are constructed partly or completely of the above mentioned low-zirconium materials, temperatures of up to a maximum of about 190° C. and pressures of up to a maximum of about 3 bar are reached. Even under these high temperatures and pressures, these materials are suitable as construction material in the presence of the extractant.

In a preferred embodiment of the invention, devices iii) and iv) are arranged in a single distillation device. The latter is generally in the form of a column.

Preferred extractants are N,N-di-n-butylformamide, N,N-di-n-butylacetamide, N-methyl-N-2-heptylformamide, N-n-butyl-N-2-ethylhexylformamide, N-n-butyl-N-cyclohexyl-formamide and/or N-ethylformanilide.

The invention also relates to the use of a low-zirconium material selected from the group consisting of the material classes titanium/palladium alloys, chromium-, molybdenum- and/or tungsten-containing nickel-based materials and molybdenum-containing, highly alloyed, austenitic chromium/nickel special steels, as construction material for the above-described apparatus.

The invention also relates to a process for obtaining anhydrous or substantially anhydrous formic acid based on a process in which, in a plant,
α) methyl formate is subjected to hydrolysis,
β) methanol and excess methyl formate are distilled off from the resultant hydrolysis mixture,
χ) the bottom product from distillation β), comprising formic acid and water, is extracted in a liquid-liquid extraction with an extractant which principally takes up the formic acid, and the extractant employed here is a carboxamide of the general formula I

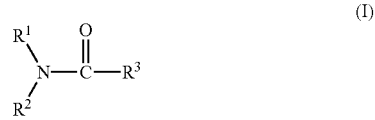

where the radicals $R^1$ and $R^2$ are alkyl, cycloalkyl, aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group,
δ) the resultant extract phase, comprising formic acid, extractant and some of the water, is subjected to distillation,
ε) the top product obtained in this distillation, which comprises water and some of the formic acid, is fed back into the lower part of the distillation device in step β),
φ)) the bottom product from distillation step δ), which comprises predominantly extractant and formic acid, is separated by distillation into anhydrous or substantially anhydrous formic acid and the extractant, and
γ) the extractant leaving step φ) is fed back into the process.

Thus, the process according to the invention is characterized in that one or more plant parts which come into contact with formic acid and with extractant are constructed partly or completely of a low-zirconium material selected from the group consisting of the material classes titanium/palladium alloys, chromium-, molybdenum- and/or tungsten-containing nickel-based materials and molybdenum-containing, highly alloyed, austenitic chromium/nickel special steels.

The temperatures during the process are on average, that means on average during all steps α) to γ) 75° C., preferably 85° C., most preferably 100° C. Especially the average temperature per step α) to γ) is in general 75° C., preferably 85° C., most preferably 100° C.

In general, the plant parts which come into contact with formic acid and with extractant are in the form of the reactor for carrying out step α), the distillation device for carrying out step β), the distillation device for carrying out step δ), the extractant device for carrying out step χ) and/or the distillation device for carrying out step φ). The extractant employed is usually N,N-di-n-butylformamide, N,N-di-n-butylacetamide, N-methyl-N-2-heptylformamide, N-n-butyl-N-2-ethyl-hexylformamide, N-n-butyl-N-cyclohexylformamide and/or N-ethylformanilide.

Figure 2:
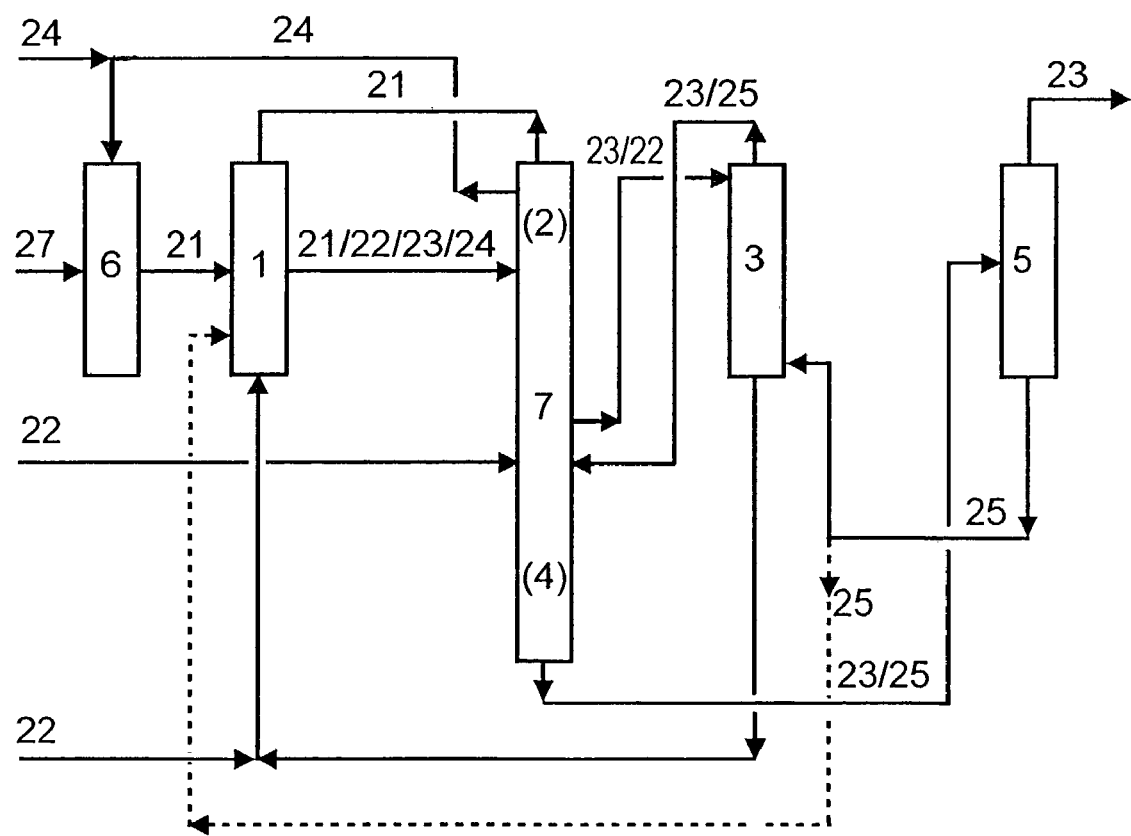

The attached drawing shows in FIG. 1 a diagram of a plant for the preparation of anhydrous or substantially anhydrous formic acid, in FIG. 2 a diagram of a plant for the preparation of anhydrous or substantially anhydrous formic acid, with the distillation device for carrying out step β) and the distillation device for carrying out step δ) are arranged in a single distillation device.

The reference numerals entered above, below or alongside the arrows indicate the components which generally have a high proportion or the principal proportion in the respective streams. Since the proportions of the components in the streams can vary, these reference numerals should only serve as guide values for information. Reference numeral 21 denotes methyl formate, 22 denotes water, 23 denotes formic acid, 24 denotes methanol, 25 denotes extractant and 27 denotes carbon monoxide. It is shown that methyl formate is prepared in a synthesis reactor 6, the hydrolysis of the methyl formate is carried out in a hydrolysis reactor 1, and step β) is carried out in a distillation device 2, the extraction is carried out in an extraction device 3, step δ) is carried out in a distillation device 4, and step φ) is carried out in a distillation device 5.

In FIG. 2, the distillation devices 2; 4 are arranged in a single distillation device 7.

The present invention will be explained in greater detail below with reference to a working example.

EXAMPLE

The extractant/anticorrosion agent employed is N,N-di-n-butylformamide. The materials studied are exposed to the corrosive medium in an autoclave. The system pressure is 3 bar, and the sample residence time is 10 days. The corresponding materials are studied with respect to their stability in seven different media. The temperatures and compositions of the mixtures indicate approximately the conditions prevailing in the process in the preparation of anhydrous or substantially anhydrous formic acid. The experimental conditions are shown in the table below.

The corrosion studies give the following results:

TABLE 9b

| Material No. | Mixture | | | | | | |
| --- | --- | --- | --- | --- | --- | --- | --- |
| | 1 | 2 | 3 | 4 | 5 | 6 | 7 |
| Class I: 3.7235 (DIN 17851) | + | + | + | + | + | + | − |
| Class II: 2.4856 (DIN 17744, EN 10095) and 2.4819 (DIN 17744) | + | + | + | + | − | + | − |
| Class III: 1.4439 (EN 10088-1-2-3, DIN 17440, DIN 17441) | − | − | + | + | − | + | − |

In the above table, a material is regarded as resistant (+) if it has a corrosion rate of less than 0.1 mm/year - otherwise, the material is denoted by (−).

The results shown in the above table indicate that materials from all three classes I to III are resistant in mixtures according to the invention containing extractants/anticorrosion agents and aqueous formic acid. It is also clear that without the use of the extractant/anticorrosion agent, the materials tested are less suitable.

We claim:

1. An apparatus for obtaining anhydrous or substantially anhydrous formic acid, at a temperature of 100° C. to 190° C., comprising i) a synthesis reactor for the preparation of methyl formate, ii) a hydrolysis reactor for the hydrolysis of the prepared methyl formate, iii) a distillation device for the separation of excess methanol and excess methyl formate from the hydrolysis mixture, iv) a distillation device for the distillation of an extract phase comprising formic acid, an extractant and some of the water, said extract phase coming from v) an extraction device for extracting the hydrolysis mixture, and vi) a distillation device for the distillative separation of a mixture comprising predominantly the extractant and formic acid coming from the distillation device iv) into anhydrous or substantially anhydrous formic acid and the extractant, TABLE 9a

| Components | Mixture 1 (aqueous phase) | Mixture 2 (organic phase) | Mixture 3 (aqueous phase with a little FA) | Mixture 4 (organic phase with a little FA) | Mixture 5 (concentrated FA in DBF, high temperature) | Mixture 6 (concentrated FA in DBF, moderate temperature) | Mixture 7 (no DBF) |
| --- | --- | --- | --- | --- | --- | --- | --- |
| FA, % by wt. | 20 | 16 | 5 | 5 | 12 | 12 | 85 |
| DBF, % by wt. | 2 | 72 | 2 | 83 | 87 | 87 | — |
| W, % by wt. | 78 | 12 | 93 | 12 | 1 | 1 | 15 |
| Temperature, ° C. | 110 | 110 | 110 | 110 | 160 | 80 | 150 |

FA = formic acid,
DBF = N,N-di-n-butylformamide,
W = water where the extractant employed is a carboxamide of the general formula I

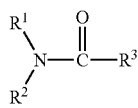 (I)

where the radicals $R^1$ and $R^2$ are alkyl, cycloalkyl. aryl or aralkyl groups, or $R^1$ and $R^2$ jointly, together with the N atom, form a heterocyclic 5- or 6-membered ring, and only one of the radicals is an aryl group, and where $R^3$ is hydrogen or a $C_1$–$C_4$-alkyl group, wherein at least one device selected from the group consisting of the devices ii), iii), iv), v) and vi) is constructed partly or entirely of a material consisting essentially of low-zirconium material containing less than 1% by weight of zirconium, and wherein the surfaces of the devices i), ii), iii), iv), v), and vi) come into contact with media which contain at least 1% of formic acid and at least 1% of the extractant.

2. The apparatus as claimed in claim 1, wherein at least one surface selected from the group consisting of the surfaces of the devices iv), v) and vi) which come into contact with media which contain at least 1% of formic acid and at least 1% of the extractant is constructed of a material consisting essentially of low-zirconium material containing less than 1% Wv weight of zirconium.

3. The apparatus as claimed in claim 2, wherein the media contains at least 1% of formic acid and at least 5% of the extractant.

4. The apparatus as claimed in claim 1, wherein devices iii) and iv) are arranged in a single distillation device.

5. The apparatus as claimed in claim 1, wherein the extractant employed is selected from the group consisting essentially of N,N-di-n-butylformamide, N-di-n-butylacetamide, N-methyl-N-2-heptylformamide, N-n-butyl-N-2-ethylhexylformamide, N-n-butyl-N-cyclobexylformamide and N-ethylformanilide.

6. The apparatus as claimed in claim 1, wherein the low-zirkonium material containing less than 1% by weight of zirconium is selected from the group consisting of the material classes titanium/palladium alloys, chromium-, molybdenum- and/or tungsten-containing nickel-based materials and molybdenum-containing, highly alloyed, austenitic chromium/nickel special steels, where the chromium-, molybdenum- and tungsten-containing nickel-based materials contain 14 to 24% by weight of Cr, 8 to 17% by weight of Mo and 3 to 5% by weight of W, max. 25% by weight of other elements and Ni as rest, the molybdenum-containing, highly alloyed, austenitic chromium/nickel special steels contain 18 to 30% by weight of Cr, 12 to 40% by weight of Ni, 3 to 7% by weight of Mo, max. 3% by weight of Cu, max. 0.05% by weight of C, max. 25% by weight of other elements and Fe as rest.

7. The apparatus as claimed in claim 1, further comprising connections between the devices (i) to (vi).

8. A process for obtaining anhydrous or substantially anhydrous formic acid, in which, in a plant,
α) methyl formate is subjected to hydrolysis,
β) methanol and excess methyl formate are distilled off from the resultant hydrolysis mixture,
χ) the bottom product from distillation β), comprising formic acid and water, is extracted in a liquid-liquid extraction with an extractant which principally takes up the formic acid, and the extractant employed here is a carboxamide of the general formula I

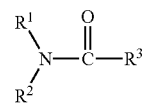 (I)

where the radicals $R^1$ and $R^2$ are alkyl, cycloalkyl, aryl or aralkyl groups, or $R^1$ and $^2$ jointly, together with the N atom, form a heterocyclic 5- or 6-membered ring, and only one of the radicals is an aryl group, and where $^3$ is hydrogen or a $C^1$–$C^4$-alkyl group,
d) the resultant extract phase, comprising formic acid, the extractant and some of the water, is subjected to distillation,
e) the top product obtained in this distillation, which comprises water and some of the formic acid, is fed back into the lower part of the distillation device in step β),
f) the bottom product from distillation step e), which comprises predominantly the extractant and formic acid, is separated by distillation into anhydrous or substantially anhydrous formic acid and the extractant, and
γ) the extractant leaving step f) is fed back into the process, wherein one or more plant parts which come into contact with formic acid and with extractant are constructed partly or completely of a material consisting essentially of low-zirconium material containing less than 1% by weight of zirconium, wherein the temperatures during the process are 100° C. to 190° C., and wherein the surfaces of the devices i), ii), iii), iv), v), and vi) come into contact with media which contain at least 1% of formic acid and at least 1% of the extractant.

9. The process as claimed in claim 8, wherein the one or more plant parts which come into contact with formic acid and with the extractant are, at least in one form selected from the group consisting of the reactor for carrying out step a), the distillation device for carrying out step β), the distillation device for carrying out step d), the extraction device for carrying out step χ) and the distillation device for carrying out step f).

10. The process as claimed in claim 8, wherein the extractant employed is selected from the group consisting of N,N-di-n-butylformamide, N,N-di-n-butylacetamide, N-methyl-N-2-heptylformamide, N-n-butyl-N-2-ethylhexylformamide, N-n-butyl-N-cyclohexylformamide and N-ethyl form-anilide.

* * * * *